United States Patent [19]
Jirkovsky

[11] Patent Number: 5,952,506
[45] Date of Patent: Sep. 14, 1999

[54] PROCESS FOR THE SYNTHESIS OF 4-[6-(HEXYLCARBAMOYLOXY) HEXYLCARBAMOYLOXY]-PIPERIDINE-1-CARBOXYLIC ACID 4-PHENOXYPHENYL ESTER

[75] Inventor: Ivo Jirkovsky, Nanuet, N.Y.

[73] Assignee: American Home Products Corporation, Madison, N.J.

[21] Appl. No.: 09/062,515

[22] Filed: Apr. 17, 1998

Related U.S. Application Data

[60] Provisional application No. 60/044,805, Apr. 24, 1997.

[51] Int. Cl.$^6$ ................................. C07D 211/46
[52] U.S. Cl. ............................................. 546/221
[58] Field of Search ............................... 546/221

[56] References Cited

FOREIGN PATENT DOCUMENTS

| 202458 | 3/1983 | Czech Rep. . |
| 508796 | 10/1992 | European Pat. Off. . |
| 550007 | 7/1993 | European Pat. Off. . |
| 575954 | 12/1993 | European Pat. Off. . |
| 635501 | 1/1995 | European Pat. Off. . |
| 111539 | 9/1977 | Japan . |

OTHER PUBLICATIONS

Katritzky, A. R. et al., "Comparative Organic Functional Group Transformations", *Pergamon*, 6:416–417.
Turconi, M. et al., *J. Med. Chem*, 33:2101–2108 (1990).
Mathison, I.W. et al., *J. Pharm Sci.*, 62:158–160 (1973).
Hobson, J.D. et al., *J. Chem. Soc.*, 2015–2017 (1967).
Cooley, J.H. et al., *Synthesis*, 1–7 (1989).
Oediger, H. et al., *Liebigs Ann. Chem.*, 764:21–27 (1972).
Campbell, A.L. et al., *Tetrahedron Letters*, vol. 28, No. 21:2331–2334 (1987).
Zabik, M.J. et al., *J. Org. Chem.*, 32:300–307 (1967).

*Primary Examiner*—Patricia L. Morris
*Attorney, Agent, or Firm*—Michael R. Nagy

[57] ABSTRACT

This invention is concerned with a new and improved process for the large scale production of 4-[6-(hexylcarbamoyloxy)hexylcarbainoyloxy]-piperidine-1-carboxylic acid 4-phenoxyphenyl ester, disclosed in European Patent Application 0 635 501 A1, published Jan. 25, 1995, a compound that inhibits cholesterol ester hydrolase (CEH) and acylcoenzyme A cholesterol acyltransferase (ACAT). In the invention process, 1-benzyl-4-hydroxypiperidine or 1-methyl-4-hydroxypiperidine is reacted with a carbonylating reagent such as carbonyldiimidazole (CDI) and 6-aminohexanol forming the intermediate 1-benzyl (or methyl)-4-(6-hydroxyhexylcarbamoyloxy) piperidine. Reaction of this intermediate with CDI and hexylamine gives the corresponding 1-benzyl (or methyl)-4-[6-(hexylcarbamoyloxy)-hexylcarbamoyloxy]piperidine. The N-benzyl or methyl group is concomitantly removed and replaced with the 4-phenoxyphenyloxycarbonyl group using 4-phenoxyphenyl chloroformate.

The process can be carried out from starting material to final product without isolation of intermediates, without changing the solvent, and the yield and purity of the final product are still more than satisfactory. This modification of the present process is clearly less labor and time intensive than the synthetic route presented in EP 0 635 501 A1.

6 Claims, No Drawings

PROCESS FOR THE SYNTHESIS OF 4-[6-(HEXYLCARBAMOYLOXY)HEXYLCARBAMOYLOXY] -PIPERIDINE-1-CARBOXYLIC ACID 4-PHENOXYPHENYL ESTER

This application claims the benefit of priority to the US provisional application No. 60/044,805 filed on Apr. 24, 1997.

FIELD OF THE INVENTION

This invention is concerned with a new and improved process for the large scale production of 4-[6-(hexylcarbamoyloxy)hexylcarbamoyloxy]-piperidine-1-carboxylic acid 4-phenoxyphenyl ester, disclosed in European Patent Application 0 635 501 A1, published Jan. 25, 1995, a compound that inhibits cholesterol ester hydrolase (CEH) and acylcoenzyme A cholesterol acyltransferase (ACAT), both enzymes that are implicated in the reesterification and absorption of exogenous cholesterol, thereby reducing cholesterol absorption. Reduction in cholesterol absorption may be useful for in the treatment of hypercholesterolemia, hyperlipidemia, and atherosclerosis.

BACKGROUND OF THE INVENTION

A multistep synthesis of 4-[6-(hexylcarbamoyloxy)hexylcarbamoyloxy]-piperidine-1-carboxylic acid 4-phenoxyphenyl ester (1) as disclosed in the cited European Patent Application is shown in Scheme I where intermediate hydroxy compounds are reacted with phosgene or a phosgene equivalent and the resultant mixed carbonic acid diesters are used to aryloxycarbonylate or alkoxycarbonylate an appropriate amine. Thus, 4-phenoxyphenol (2) is treated with 4-nitrophenyl chloroformate (NPC) and condensation of the corresponding carbonate (3) with 4-hydroxypiperidine affords 4-hydroxy-1-piperidine-carboxylic acid 4-phenoxyphenyl ester (4). Repeating the NPC activation step with the latter intermediate and the following condensation of carbonate (5) with 6-aminohexanol yield 4-[(6-hydroxyhexyl)carbamoyloxy]-piperidine-1-carboxylic acid 4phenoxyphenyl ester (6). To complete the synthesis of (1), the alcoholic function of this intermediate is activated again with NPC and treated with hexylamine, or reacted directly with hexylisocyanate.

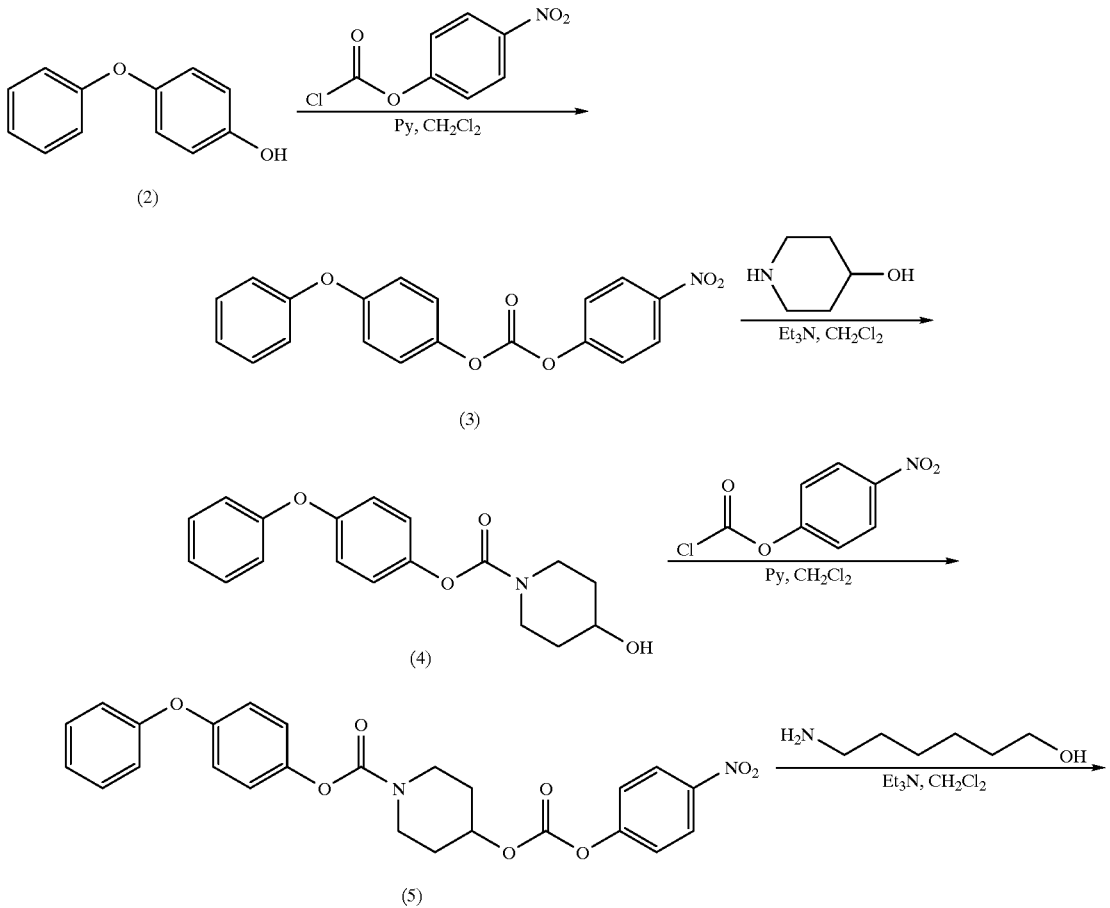

Scheme I

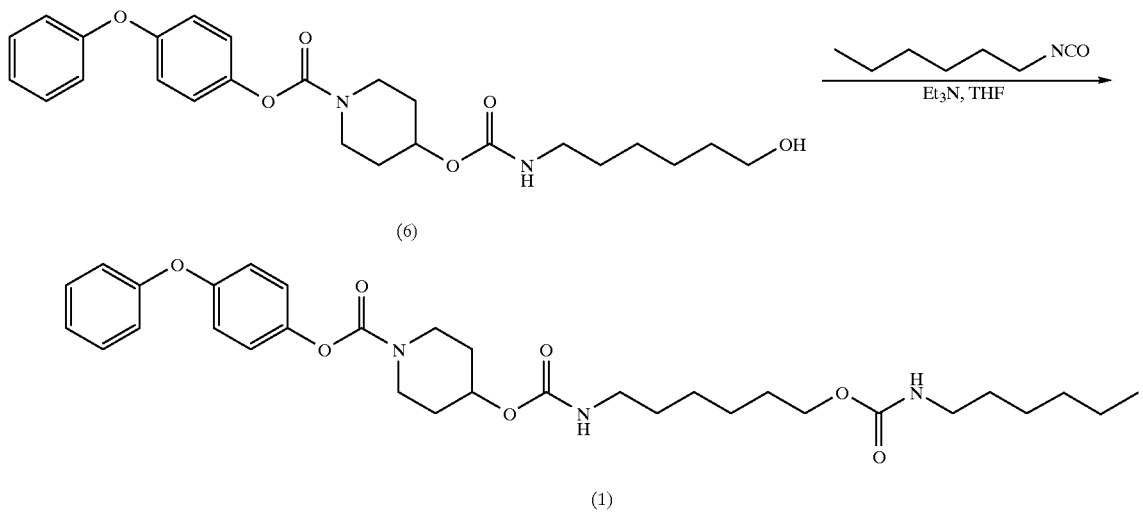

Although useful for laboratory preparations, the above described synthesis of the title compound is less suitable for a commercial scale process. Obvious disadvantages include high cost of reagents (NPC and hexylisocyanate), a necessary recrystallization of intermediates, and a modest overall yield. Moreover, small amounts of by-products, such as symmetrical carbonates, carbamate-carbonates and ureas form in each step, and these impurities accumulate to make crystallization of the final product difficult. Additionally, the (4-phenoxy) -phenoxycarbonyl group is not completely inert under the described reaction conditions. The prior art patent application suggests the benzyloxycarbonyl moiety as an alternative, removable N-protecting group, however, the syntheses of the title compound from 1-benzyloxycarbonyl-4-hydroxypiperidine or analogous N-carbonylated species does not give a significantly better profile of impurities in the crude final product than when the phenoxyphenyl carbamate ester of 4-piperidinol is formed in the first step of the reaction sequence (Scheme I).

SUMMARY OF THE INVENTION

The invention provides a new process for the large scale production of 4-[6 -(hexylcarbamoyloxy) hexylcarbamoyloxy]-piperidine-1-carboxylic acid 4-phenoxyphenyl ester of the formula (1) as outlined in Scheme II.

tions of the new process are shown in Scheme II wherein R is either benzyl or methyl. The starting materials, 1-benzyl-4-hydroxypiperidine or 1-methyl-4 -hydroxypiperidine (7) are less expensive than 4-hydroxypiperidine as used in Scheme I. The sequence of steps begins with reacting 1-substituted-4-hydroxypiperidines (7) with a carbonylating reagent such as carbonyl diimidazole (CDI), disuccinimidyl carbonate, 2,2'-carbonyl-bis(3,5-dioxo-1,2,4-oxazolidine or 3,3'-carbonyl-bis[5-phenyl- 1,3,4-oxadiazole-2(3H)thione], preferably carbonyl diimidazole, and subsequently coupling the reactive intermediate thus formed with 6-aminohexanol provides intermediate hydroxycarbamates (8) that are in turn subjected to carbonylation and coupling with hexylamine. The resultant intermediates (9) represent two heretofore unknown compounds which can be readily isolated and purified by crystallization.

Having served their purpose as "protecting groups," the N-benzyl or N-methyl substituents are removed in the last step by dealkylation with concomitant aryloxycarbonylation. This conversion (Scheme II) into the final product (1) is achieved by treatment of (9) with 4phenoxyphenyl carbonochloridate (4-phenoxyphenyl chloroformate) (10). The reaction proceeds surprisingly smoothly and affords material of high purity.

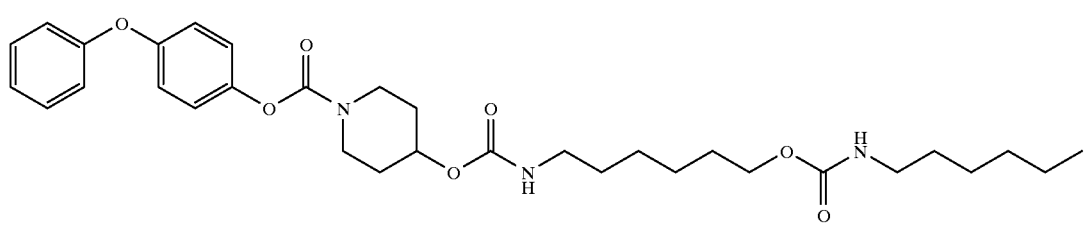

(1)

Characterized by improved purity of the product, higher yields, lower costs, and technical convenience, two varia-

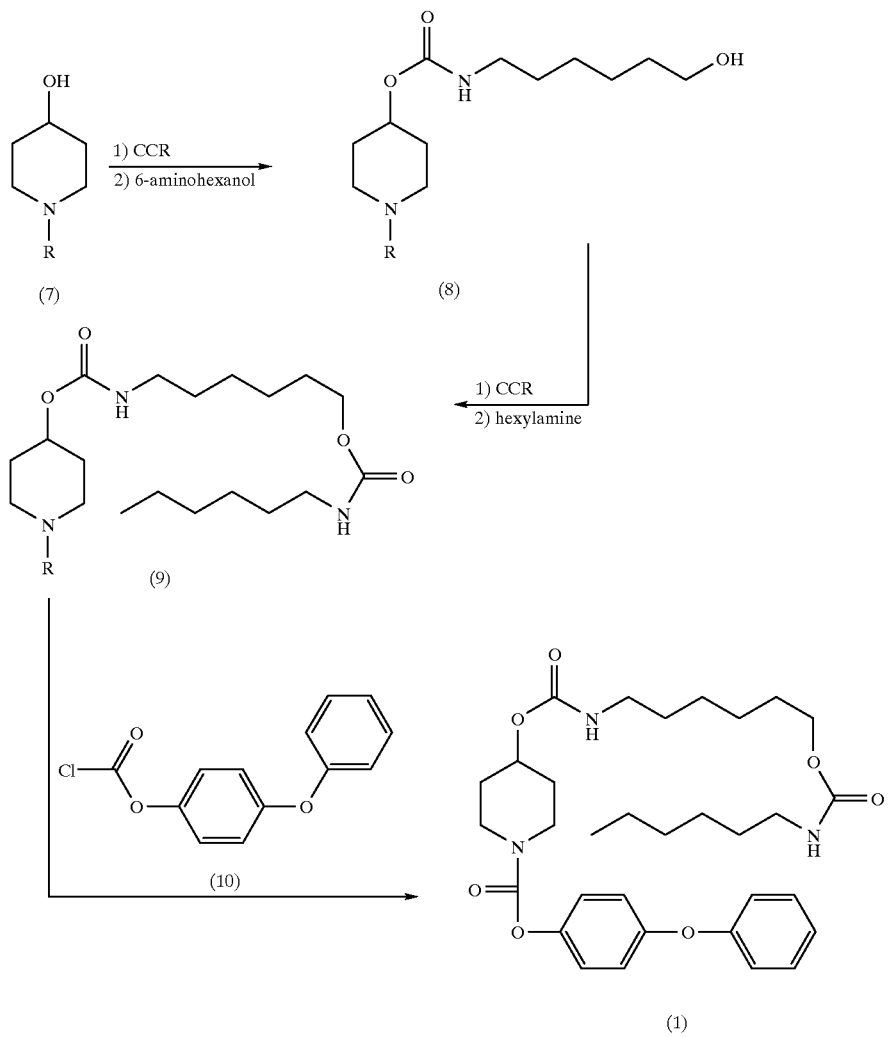

R = benzyl or methyl
CCR = coupling carbonylation reagent, e.g., N, N'-carbonyldiimidazole

DETAILED DESCRIPTION OF INVENTION

A general method for preparation of carbamates by sequential reaction of alcohols with N,N'-carbonyldidazole (CDI) and an amine is outlined in *Comprehensive Organic Functional Group Transformations;* A. R. Katritzky, O. Meth-Cohn, C. W. Rees, Ed.; Pergamon; Vol. 6, pages 416–7.

For more recent examples of this methodology see European patents EP 508796, EP 550007 and EP 575954. However, there is no report in the literature that describes activation of 1-substituted-4-hydroxypiperidines with CDI and the following alkoxycarbonylation of an amine.

The carbonylation coupling reaction sequence is extremely useful for the conversion of (7) to (8). The reactive intermediate formed upon treating 1-substituted-4-piperidinol (7) with carbonyldiimidazole, presumably (1-substituted-4-piperidinyl) imidazole-1'-carboxylic acid ester, offers excellent selectivity in reacting preferentially with primary amino group over primary hydroxyl groups, and results in significantly higher yields and higher purity of tje product (8) than analogous methodology employing 1-methyl-piperidin-4-yl chloroformate (J. Med. Chem. 1990, 33, 2101) or any 1-alkyl-piperidin-3-yl chloroformate (J. Pharm. Sci. 1973, 62, 158). Thus, for the process described in Scheme II, specifically for the transformations (7) to (8) and (8) to (9), CDI is an excellent substitute for phosgene.

The reaction of hydroxypiperidines (7) with CDI and 6-aminohexanol, as well as the reaction of (8) with CDI and hexylamine are carried out in an aprotic solvent such as tetrahydrofuran, toluene, methylene chloride, or ethyl acetate at from about 0° C. to about 70° C. or to the boiling point of the solvent used if lower than 70° C. in the absence or presence of a tertiary amine, preferably triethylamine. As a strong Lewis base, triethylamine causes a substantial decrease in the reaction time, and the carbarnates (8 and 9) are obtained in higher yield and purity. In the case of 1-methyl-4-hydroxypiperidine, acceptable yields are achieved only in the presence of triethylamine.

The penultimate intermediate carbamates (9) can be recrystallized from a variety of solvent systems, for example, acetone, acetone/heptane, ethyl acetate, aqueous tetrahydrofuran, or ether.

Cleavage of tertiary amines by reaction with chloroformates is well known. The superiority of phenyl chloroformate over methyl chloroformate and ethyl chloroformate has been reported (J.Chem.Soc.(C) 1967, 2015), the development of this reaction has been reviewed (Synthesis 1989, 1–7), and an application of the method to 1,2,5,6-tetrahydropyridines has been described (Liebigs Ann. Chem. 764, 21–27, 1972). The closest prior art to the present invention is debenzylation of an acetal derived from 1-benzyl-4-hydroxypiperidine with β-trimethyl-silylethyl chloroformate (Tetrahedron Lett. 1987, 2331). To date, there is no example in the literature of dealkylating a tertiary amine in the presence of carbamoyl groups and using an aryl chloroformate of higher molecular weight than phenyl chloroformate, e.g., 4-phenoxyphenyl chloroformate (10). It is therefore surprising that the conversion of (9) to the title compound (1) proceeds smoothly without significant or even appreciable side-reactions or alternative fragmentation, in essentially quantitative crude yield.

Dealkylation of (9) with concomitant N-(4-phenoxy) phenoxycarbonylation is carried out at temperatures between about 15° C. and about 110° C., preferably in toluene, however, chlorinated solvents such as methylene chloride and 1,2-dichloroethane, or dimethyl formamide, are also suitable. Both the debenzylation and the demethylation of (9), where R is benzyl or methyl, can be accomplished in a high yield. However, the demethylation procedure releases volatile and toxic methyl chloride and is less preferred and less environmentally friendly.

The requisite 4-phenoxyphenyl chloroformate (10) is heretofore an unknown compound. It is conveniently prepared by a procedure analogous to the prior art method (J. Org. Chem. 1967, 32, 300; Japanese patent JP 76-27090; Czechoslovakia patent CS 202458) which comprises reaction of phosgene with 4-phenoxyphenol in the presence of N,N-dimethyl or N,N-diethylaniline, preferably in toluene. To quantify 4-phenoxyphenyl chloroformate formed, an aliquot sample is treated with isopropanol and the content of the corresponding mixed carbonate is determined by GC or HPLC methods.

It is noteworthy that the process diagramed in Scheme II can be carried out from starting material (7) to final product (1) without isolation of intermediates, without changing the solvent (preferably toluene), and the yield and purity of (1) are still more than satisfactory. This modification of the present process is clearly less labor and time intensive than the synthetic route presented in EP 0 635 501 A1.

The following examples illustrate the process of the present invention.

EXAMPLE 1
N-(6-Hydroxyhexyl)carbamic acid (1-benzyl-4-piperidinyl) ester (8; R=benzyl)

A stirred suspension of N,N'-carbonyldiimidazole (3.24 g, 20 mmol) in The (40 mL) was warmed up to 50° C., and a solution of 1-benzyl-4-hydroxypiperidine (3.82 g, 20 mmol) in THF (17 mL) was added dropwise over 10 min. Stirring was continued for 2 hrs. at room temperature (RT), and a solution of 6-aminohexanol (3.50 g, 30 mmol) and triethylamine (3.04 g, 30 mmol) in THF (40 mL) was added dropwise over 10 min. When the reaction mixture turned cloudy, the rate of stirring was increased, and a clear solution was obtained within 20–30 min. The mixture was refluxed for 2 hrs., concentrated in vacuo, and the residue was partitioned between ether (70 mL) and water (35 mL). An alternative partitioning between ethyl acetate and water was equally effective. The organic layer was washed with brine, dried over magnesium sulfate, filtered, and evaporated to give the title compound (6.68 g, yield 100%) as a light, yellowish oil. TLC (chloroform-5% methanol) showed a single spot at $R_f$ 0.5; $^1$H NMR (300 MHz, CDCl$_3$) δ1.37 (m, 4H, CH$_2$), 1.47–1.61 (m, 4H, CH$_2$), 1.67 (m, 2H, CH$_2$, piperidine ring axial protons), 1.88 (m, 2H, CH$_2$, piperidine ring equatorial protons), 2.22 (t, J=9 Hz, 2H, CH—N—CH, piperidine ring axial protons), 2.69 (m, 2H, CH—N—CH, piperidine ring eq. protons), 3.16 (q, J=6.5 Hz, 2H, CH$_2$—NH), 3.49 (s, 2H, CH$_2$—Ph), 3.62 (t, J=6.5 Hz, 2H, CH$_2$—O), 4.66 (m, 1H, CH—O), 4.73 (t, J=6 Hz, 1H, NH), 7.23–733 (m, 5H, Ar—H).

EXAMPLE 2
1-Benzyl-4-[6-(hexylcarbamoyloxy)hexylcarbamoyloxy] piperidine (9, R=benzyl)

A solution of the intermediate carbinol (8) from Example 1 (6.68 g, 20 mmol) in THF (30 mL) was added dropwise to a stirred suspension of N,N'-carbonyldiimidazole (3.24 g, 20 mmol) in THF (40 mL) at 50° C. Stirring was continued for 2 hrs. at RT, and the resulting clear solution was treated with a solution of hexylamine (2.02 g, 20 mmol) and triethylamine (2.02 g, 20 mmol) in THF (20 mL). The reaction mixture was stirred for 30 min. at RT, heated to reflux for 2 hrs., and evaporated in vacuo. The residue was partitioned between ethyl acetate and water, the separated organic phase was washed with brine, dried over magnesium sulfate, filtered, and concentrated to give the title bis-carbamate as a crystalline material in three crops; a total of 8.2 g (89%) was collected by filtration, m.p. 79–80° C.

Two alternative work-ups of the reaction mixture were found equally effective: pouring a concentrated ThF solution into vigorously stirred ice water and collecting the crystalline product by filtration, or evaporation of THF followed by extraction with ether, and crystallization of the crude product from acetone-heptane, m.p. 79–80° C.

TLC (chloroform-3% methanol) $R_f$ 0.35; $^1$H NMR (300 MHz, CDCl$_3$) δ0.88 (t, J=6.5 Hz, 3H, CH$_3$), 1.28 (m, 4H, CH$_2$), 1.36 (m, 4H, CH$_2$), 1.49 (m, 4H, CH$_2$), 1.55–1.72 (m,6H, CH$_2$), 1.89 (m, 2H, CH$_2$), 2.22 (t, J=9 Hz, 2H, CH—N—CH), 2.68 (m, 2H, CH—N—CH), 3.15 (q, J=6.5 Hz, 4H, CH$_2$—NH), 3.49 (s, 2H, CH$_2$—Ph), 4.03 (t, J=6.5 Hz, 2H, CH$_2$—O),4.5 and 4.66 (br, 1H+2H, NH and CH—O), 7.23–7.33 (m, 5H, Ar—H); MS (CI) 462 (MH$^+$, 75), 372 (33), 335 (46), 271 (100), 245 (44), 192 (62), 174 (96).

EXAMPLE 3
1-Benzyl-4-[6-(hexylcarbamoyloxy)hexylcarbamoyloxy] piperidine (9, R=benzyl)
{in the absence of triethylamine and without isolation of the intermediate}

A stirred suspension of N,N'-carbonyldiimidazole (58.38 g, 0.36 mol) in methylene chloride (250 mL) was treated with a solution of 1-benzyl-4-hydroxypiperidine (57.80 g, 0.30 mol) in the same solvent (200 mL) at RT. The resulting clear solution was stirred for 2 hrs., washed 3 times with water (60 mL), and the organic phase was added into a solution of 6-aminohexanol (52.8 g, 0.45 mol) in methylene chloride (150 mL). The reaction mixture was kept overnight at RT, washed with water, dried over magnesium sulfate, filtered, and concentrated. Comparative TLC confirmed that the product was identical to the intermediate carbamate prepared according to Example 1. The material was redissolved in methylene chloride (110 mL) and added to a stirred suspension of N,N'-carbonyldiimidazole (53.50 g, 0.33 mol) in the same solvent (250 mL). The resulting solution was kept for 1 hr. at RT, and then mixed with a solution of hexylamine (60 mL, approx. 1.5 eq.) in methylene chloride (60 mL). The reaction mixture was stirred overnight at RT, washed with water, dried over magnesium sulfate, filtered, and evaporated to give waxy, semi-solid residue. The contents of the flask were slurried in t-butyl-methyl ether (200 mL) and the first crop of crystals collected by filtration. Another crop of crystalline product was obtained upon addition of heptane to the filtrate. The product (111.95 g, 80%), m.p. 78–80° C., was identical with the carbamate prepared according to Example 2.

EXAMPLE 4

4-Phenoxyphenyl chloroformate (10)

A solution of 4-phenoxyphenol (1.12 g, 6 mmol) in toluene (15 mL) was cooled to −10° C., and 4.2 mL of 1.93M solution of phosgene in toluene (0.8 g, 8 mmol) was added at once. The mixture was stirred at −10° C. and a solution of N,N-diethylaniline (0.99 g, 6.6 mmol) in toluene (5 mL) was added dropwise. The reaction mixture was allowed to reach RT over the next 2 hrs., and the precipitated salt was filtered off. To remove an excess of phosgene, the filtrate was sparged with nitrogen for 20 min.

A small aliquot sample of the toluene solution was treated with a drop of isopropanol to convert the chloroformate into the corresponding carbonate, and the amount of 4-phenoxyphenyl isopropyl carbonate was determined by GC/MS. The product analysis showed that the 4-phenoxyphenyl chloroformate contained 0.9% of the starting 4-phenoxyphenol. MS for isopropyl 4-phenoxyphenyl carbonate: 272 (10), 213 (11), 187 (13), 186 (100), 185 (13).

EXAMPLE 5

4-[6-(Hexylcarbamoyloxy)hexylcarbamoyloxy]-piperidine-1-carboxylic acid 4 -phenoxyphenyl ester (1)
{by N-debenzylation}

The toluene solution of 4-phenoxyphenyl chloroformate (10) prepared according to Example 4 was added to a solution of the biscarbamate (9) (2.69 g, 5.83 mmol) prepared in Example 2 in toluene (16 mL), and the reaction mixture was heated at 100° C. for 4 hrs. A mild vacuum was applied intermittently during the final 2 hrs. to distill off some 20 ml of toluene. After cooling, the mixture was diluted with toluene (15 mL), and washed successively with 0.5N NaOH, 0.5N HCl, water, brine. The organic phase was dried over magnesium sulfate, filtered, and evaporated. The solidified product was recrystallized from n-butanol/heptane to give 3.0 g (88%) of the title compound (1); m.p. 79.5–79.9° C.

TLC (chloroform-3% methanol) $R_f$0.65; $^1$H NMR (300 MHz, CDCl$_3$) δ8 0.88 (t, J=6.5 Hz, 3H, CH$_3$), 1.29 (m, 4H, CH$_2$), 1.37 (m, 4H, CH$_2$), 1.46–1.52 (m, 6H, CH$_2$ ), 162 (m, 2H, CH$_2$), 1.69 (m, 2H, CH$_2$), 1.95 (m, 2H, CH$_2$), 3.18 (m, 4H, CH$_2$—NH), 3.42 and 3.88 (br m, 4H, CH$_2$—N—CH$_2$, ring protons), 4.04 (t, J=6.5 Hz, CH$_2$—O), 4.67 (m, 1H, CH—O), 4.71 and 4.89 (br, 1H+1H, NH), 7.00 and 7.05 (m, 7H, Ar—H), 7.32 (m, 2H, Ar—H); MS (LC/CI) 584 (MH$^+$, weak), peak of highest abundance m/z 314.

EXAMPLE 6

1-Methyl-4-[6-hexylcarbamoyloxy)hexylcarbamoyloxy] piperidine (9, R=methyl)
{without isolation of the intermediate N-(6-hydroxyhexyl) carbamic acid (1-methyl4-piperidinyl) ester (8)}

A solution of 1-methyl-4-hydroxypiperidine (1.15 g, 10 mmol) and triethylamine (1.01 g, 10 mmol) in THF (8mL) was kept 6 hrs. at RT, and then was added to a stirred suspension of N,N'-carbonyldiimidazole (1.62 g, 10 mmol) in THF (20 mL) at 50° C. Stirring at RT was continued for 2 hrs. The reaction mixture was then heated to reflux for 3 hrs., and allowed to cool. A solution of 6-aminohexanol (1.75 g, 15 mmol) and triethylamine (1.52 g, 15 mmol) in THF (40 ml) was added dropwise over 15 min. The resulting solution was refluxed for 3 hrs., evaporated in vacuo, and the residue was partitioned between ethyl acetate (50 mL) and water (10 mL). The organic layer was separated, washed with brine, dried over magnesium sulfate, and filtered. The volatiles were removed on a rotavapor to give 2.48 g (96%) of the intermediate carbinol (8) as yellowish oil. TLC (ethyl acetate/methanol 3:1; visualization in iodine chamber) showed a major spot with $R_f$0.25; LC/MS(CI): area 90%; m/z 259 (MH$^+$).

A solution of this intermediate (2.12 g, 7.34 mmol assuming 90% strength) in ThF (17 mL) was added to a stirred suspension of N,N'-carbonyldiimidazole (1.19 g, 7.34 mmol) in THF at 45° C. The resulting clear solution was stirred for 30 min., and a solution of hexylamine (0.74 g, 7.32 mmol) and triethylamine (0.74 g, 7.32 mmol) in THF (5 mL) was added rapidly. The reaction mixture was refluxed for 3 hrs., concentrated in vacuo, the residual material was redissolved in ether (60 mL), and filtered. The filtrate was evaporated in vacuo, and the residue was crystallized from acetone/heptane to give 1.8 g (70%) of the title compound, m.p. 84–87° C.

TLC (chloroform-5% methanol) $R_f$0.35; $^1$H NMR (300 MHz, CDCl$_3$) δ0.88 (t, J=6.5 Hz, 3H, CH$_3$), 1.28 (m, 4H, CH$_2$), 1.36 (m, 4H, CH$_2$), 1.46 (m, 4H, CH$_2$), 159 and 168 (m, 5H, CH$_2$), 1.89 and 1.99 (m, 3H, CH$_2$), 2.21 (m, 2H, CH—N—CH, piperidine ring axial protons), 2.26 (s, 3H, N—CH$_3$), 2.63 (m, 2H, CH—N—CH, piperidine ring equatorial protons), 3.14 (q, J=6.5 Hz, 4H, CH$_2$—NH), 4.03 (t, J=6 Hz, 2H, CH$_2$—O), 4.64 (m, 1H, CH—O), 4.71 (br, 2H, NH).

EXAMPLE 7

4-[6-(Hexylcarbamoyloxy)hexylcarbamoyloxy]-piperidine-1-carboxylic acid 4 -phenoxyphenyl ester (1)
{by N-demethylation}

The toluene solution of 4-phenoxyphenyl chloroformate (10) prepared according to Example 4 was added to a solution of the biscarbamate (9)(2.23 g, 5.80 mmol) prepared in Example 6) in the same solvent (15 mL). The resultant milky solution was refluxed for 5 hrs. using a Dean-Stark separator, and eventually more toluene was removed under mild vacuum. After cooling, the reaction mixture was diluted with toluene, washed successively with 1N HCl, 1N NaOH, water, and brine. The organic phase was dried over magnesium sulfate, filtered, and evaporated under reduced pressure to obtain a solid residue (3.1 g, 91.9%; m.p. 78–79° C.). HPLC analysis of the solid residue showed only small amounts of impurities, and one crystallization of this material from n-butanol/heptane afforded pure title compound, m.p. 79.4–80° C.; TLC and spectra identical with those described in Example 5.

EXAMPLE 8

4-[6-(Hexylcarbamoyloxy)hexylcarbamoyloxy]-piperidine-1-carboxylic acid 4 -phenoxyphenyl ester (1)
{by N-debenzylation and without isolation of intermediates (8–9)}

A stirred suspension of N,N'-carbonyldiimidazole (1.62 g,10 mmol) in toluene (20 mL) was treated dropwise with a solution of 1-benzyl-4-hydroxypiperidine (1.91 g,10 mmol) in the same solvent (10 ml) at 50° C. The resulting solution was stirred at 50–55° C. for 2.5 hrs. and a warm solution of 6-aminohexanol (1.63 g, 14 mmol) and triethylamine (1.41 g, 14 mmol) in toluene (25 mL) was added, and the mixture was stirred at 55° C. overnight. After cooling, the mixture was washed with water and brine, dried over magnesium sulfate, and filtered with the filtrate directed into a suspension of N,N'-carbonyldiimidazole (1.62 g, 10 mmol) in toluene (20 ml) at 50° C. The resulting mixture was stirred at 55° C. for 2 hrs. and a solution of hexylamine (1.01 g, 10 mmol) and triethylamine (1.01 g, 10 mmol) in toluene (5 mL) was added portionwise over 5 min. Heating at 55° C. was continued for 4 hrs. After cooling, the contents of the flask were transferred to a separatory funnel and washed twice with water and brine. The organic phase was dried over magnesium sulfate, filtered, and mixed with a toluene solution of 4-phenoxyphenyl chloroformate prepared according to Example 4 from 4-phenoxyphenol (1.86 g, 10 mmol). This mixture was kept at RT overnight, then concentrated under reduced pressure, and diluted with heptane. The solid product was collected by filtration, and recrystallized twice from n-butanol/heptane to give the title compound (1) as crystalline material, m.p. 79–80° C.; 3.9 g (66.9%); TLC, HPLC, and spectra are identical with those described in Example 5.

What is claimed is:

1. A process for the preparation of 4-[6-hexylcarbamoyloxy)hexylcarbamoyloxy]-piperidine-1-carboxylic acid 4-phenoxyphenyl ester which comprises:
    a) reacting 1-benzyl-4-hydroxypiperidine or 1-methyl-4-hydroxypiperidine with (i) a carbonylating coupling reagent selected from the group consisting of carbonyldiimidazole, disuccinimdyl carbonate, 2,2'-carbonyl-bis (3.5-dioxo-1,2,4-oxazolidine) and 3,3'-carbonyl-bis[5-phenyl-1,3,4-oxadizaole-2(3H)thione] and (ii) 6-aminohexanol in an aprotic solvent at 0–70° C. with a tertiary amine optionally present;
    b) reacting the resultant 4-[(6-hydroxyhexyl) carbamoyloxy]piperidine with (i) a carbonylating coupling reagent selected from the group consisting of carbonyldiimidazole, disuccinimdyl carbonate, 2,2'-carbonyl-bis(3,5-dioxo1,2,4-oxazolidine) and 3,3'-carbonyl-bis[5-phenyl-1,3,4-oxadizaole-2(3H)thione] and (ii) hexylamine in an aprotic solvent at 0–70° C. with a tertiary amine optionally present; and
    c) dealkylation and concomitant N-(4-phenoxy) phenoxycarbonylation of the intermediate 4-[6-(hexylcarbamoyloxy)hexylcarbamoyloxy]piperidine with 4-phenoxyphenyl chloroformate in an aprotic solvent at 15–110° C.

2. A process according to claim 1 wherein the carbonylating coupling reagent is carbonyldiimidazole and the reactions are carried out in the presence of triethylamine.

3. The process according to claim 1 wherein the aprotic solvent used is toluene.

4. The process according to claim 1, wherein the intermediate formed is:
    1-benzyl-4-[(6-hydroxyhexyl)carbamoyloxy]piperidine,
    1-methyl-4-[(6-hydroxyhexyl)carbamoyloxy]piperidine,
    1-benzyl-4-[6-(hexylcarbamoyloxy)hexylcarbamoyloxy] piperidine, or
    1-methyl-4-[6-(hexylcarbamoyloxy)hexylcarbamoyloxy] piperidine.

5. A process for the preparation of 4-[6-(hexylcarbamoyloxy)hexylcarbamoyloxy]-piperidine-1-carboxylic acid 4-phenoxyphenyl ester which comprises dealkylation and concomitant N-(4-phenoxy) phenoxycarbonylation of 1-benzyl (or methyl)-4-[6-(hexylcarbamoyloxy)hexylcarbamoyloxy]piperidine with 4-phenoxyphenyl chloroformate in an aprotic solvent at 15–110° C.

6. The process according to claim 5 wherein the solvent used is toluene.

* * * * *